US010596556B2

(12) United States Patent
Radivojevic et al.

(10) Patent No.: US 10,596,556 B2
(45) Date of Patent: Mar. 24, 2020

(54) SURFACE MODIFIED METALLIC FOAM BODY, PROCESS FOR ITS PRODUCTION AND USE THEREOF

(71) Applicants: Alantum Europe GmbH, Munich (DE); FRAUNHOFER GESELLSCHAFT ZUR FORDERUNG DER ANGEWANDTEN FORSCHUNG E.V., München (DE)

(72) Inventors: Dejan Radivojevic, Vienna (AT); Dirk Neumann, Cherry Valley (CA); Shadi Saberi, Kanata (CA); Jungsuk Bae, Seoul (KR); Rene Poss, Hanau (DE); Tilo Büttner, Dresden (DE); Gunnar Walther, Dresden (DE); Hans-Dietrich Böhm, Dresden (DE); Thomas Weissgärber, Dresden (DE); Burghardt Klöden, Dresden (DE); Arne Boden, Dresden (DE)

(73) Assignees: Alantum Europe GmbH, Munich (DE); FRAUNHOFER GESELLSCHAFT ZUR FORDERUNG DER ANGEWANDTEN FORSCHUNG E.V., Munich (DE)

( * ) Notice: Subject to any disclaimer, the term of this patent is extended or adjusted under 35 U.S.C. 154(b) by 983 days.

(21) Appl. No.: 14/173,312

(22) Filed: Feb. 5, 2014

(65) Prior Publication Data

US 2014/0221700 A1    Aug. 7, 2014

(30) Foreign Application Priority Data

Feb. 6, 2013    (EP) ..................... 13154293

(51) Int. Cl.
| | | |
|---|---|---|
| B01J 23/00 | (2006.01) | |
| B01J 25/02 | (2006.01) | |
| C07C 29/136 | (2006.01) | |
| B01J 35/10 | (2006.01) | |
| B01J 37/02 | (2006.01) | |
| B01J 37/08 | (2006.01) | |
| B01J 37/18 | (2006.01) | |
| B01J 35/04 | (2006.01) | |
| B01J 37/00 | (2006.01) | |
| C22C 1/08 | (2006.01) | |
| B01J 23/755 | (2006.01) | |

(52) U.S. Cl.
CPC .............. *B01J 25/02* (2013.01); *B01J 35/04* (2013.01); *B01J 35/10* (2013.01); *B01J 35/1014* (2013.01); *B01J 37/0018* (2013.01); *B01J 37/0215* (2013.01); *B01J 37/0217* (2013.01); *B01J 37/0225* (2013.01); *B01J 37/08* (2013.01); *B01J 37/18* (2013.01); *C07C 29/136* (2013.01); *C22C 1/08* (2013.01); *B01J 23/755* (2013.01)

(58) Field of Classification Search
CPC ........ B01J 25/02; B01J 35/10; B01J 35/1014; B01J 35/04; B01J 37/0215; B01J 37/0225; B01J 37/0217; B01J 37/18; B01J 37/08; B01J 37/0018; B01J 23/755; C22C 1/08; C07C 29/136
USPC ........ 502/325; 204/284, 290, 292, 206, 287, 204/252; 429/220, 223, 233, 235, 236, 429/237, 241; 428/566, 567, 613; 205/161, 264, 271, 291, 333, 236, 255
See application file for complete search history.

(56) References Cited

U.S. PATENT DOCUMENTS

| | | |
|---|---|---|
| 2,895,819 A | 7/1959 | Stuart |
| 3,126,273 A | 3/1964 | Justi et al. |
| 3,637,437 A | 1/1972 | Goldberger et al. |
| 4,049,580 A | 9/1977 | Oden et al. |
| 5,848,351 A | 12/1998 | Hoshino et al. |
| 6,051,117 A | 4/2000 | Novak et al. |
| 6,117,592 A | 9/2000 | Hoshino et al. |
| 6,486,366 B1 | 11/2002 | Ostgard et al. |
| 6,747,180 B2 | 6/2004 | Ostgard et al. |
| 6,926,969 B2 | 8/2005 | Bohm et al. |
| 7,108,828 B2 | 9/2006 | Lefebvre et al. |
| 7,951,246 B2 | 5/2011 | Naumann et al. |

(Continued)

FOREIGN PATENT DOCUMENTS

| | | |
|---|---|---|
| CN | 101537360 A | 9/2009 |
| CN | 101537361 A | 9/2009 |

(Continued)

OTHER PUBLICATIONS

Communication dated Apr. 8, 2016, from the State Intellectual Property Office of People's Republic of China in counterpart application No. 201410045131.1.

(Continued)

*Primary Examiner* — Haytham Soliman
(74) *Attorney, Agent, or Firm* — Sughrue Mion, PLLC

(57) ABSTRACT

A metallic foam body containing an alloy skin which is up to 50 μm thick can be obtained by a process including (a) providing a metallic foam body comprising a first metallic material; (b) applying a second metallic material which contains a first metallic compound that is leachable as such and/or that can be transformed by alloying into a second metallic compound that is leachable and different from the first metallic compound on a surface of the foam body (a), by coating the metallic foam body with an organic binder and a powder of the second metallic material; (c) forming a skin on foam body (b) by alloying the first and the second metallic material; and (d) leaching out with a leaching agent at least a part of the first and/or the second metallic compound.

18 Claims, No Drawings

(56) References Cited

U.S. PATENT DOCUMENTS

| | | |
|---|---|---|
| 8,012,598 B2 | 9/2011 | Naumann et al. |
| 2008/0171218 A1 | 7/2008 | Naumann et al. |
| 2009/0018366 A1 | 1/2009 | Berweiler et al. |
| 2010/0055516 A1 | 3/2010 | Mason et al. |

FOREIGN PATENT DOCUMENTS

| | | |
|---|---|---|
| CN | 101549297 A | 10/2009 |
| DE | 199 33 450 A1 | 1/2001 |
| JP | 1-184206 A | 7/1989 |
| JP | 07-206737 A | 8/1995 |
| JP | 2001-54735 A | 2/2001 |
| JP | 2005-205265 A | 8/2005 |
| JP | 2007-527954 A | 10/2007 |
| JP | 2012-111988 A | 6/2012 |
| JP | 2012-124012 A | 6/2012 |
| WO | 2005/095029 A2 | 10/2005 |

OTHER PUBLICATIONS

B. Monnerat et al., "Hydrogen production by catalytic cracking of methane over nickel gauze under periodic reactor operation", Chemical Engineering Science, 2001, pp. 633-639, vol. 56.

Hao Lei et al., "Preparation of novel Raney-Ni catalysts and characterization by XRD, SEM and XPS", Applied Catalysis A: General, 2001, pp. 69-76, vol. 214.

Rectical Company Brochure, "The Guide 2000 of Technical Foams", Book 4, Part 4, pp. 33-41.

L. Salvo et al., "X-ray micro-tomography an attractive characterisation technique in materials science", Nuclear Instruments and Methods in Physics Research B, 2003, pp. 273-286, vol. 200.

F. Devred et al., "The genesis of the active phase in Raney-type catalysts: the role of leaching parameters", Applied Catalysis A: General, 2003, pp. 291-300, vol. 244.

B. Grushkoa et al., "A study of the Al-rich region of the Al—Ni—Mo alloy system", Journal of Alloys and Compounds, 2002, pp. 187-191, vol. 334.

Eun-Ey Jung et al., "Effects of Catalytic Activity on Promotor Doped Raney Nickel", Journal of Ind. & Eng. Chemistry, Mar. 1997, pp. 24-28, vol. 3, No. 1.

I. Yuranov et al., "Metal grids with high-porous surface as structured catalysts: preparation, characterization and activity in propane total oxidation", Applied Catalysis B: Environmental, 2002, pp. 183-191, vol. 36.

Japanese Patent Office; Communication dated Sep. 13, 2016 in counterpart application No. 2015-556485.

Chinese Patent Office, Communication dated Nov. 21, 2016 in corresponding Chinese Application No. 201410045131.1.

Intellectual Property India: Communication dated Dec. 1, 2018 in application No. 6955/DELNP/2015.

SURFACE MODIFIED METALLIC FOAM BODY, PROCESS FOR ITS PRODUCTION AND USE THEREOF

The invention relates to a surface modified metallic foam body, a process for its production and a use of the surface modified metallic foam body.

Raney catalysts are often used in powder form for performing the hydrogenation of various compounds, for example the hydrogenation of carbonyl compounds. Raney catalysts which are also called activated, sponge or skeletal metal catalysts are made of an alloy of at least one catalytically active metal and at least one metal that can be leached out by alkalis. Aluminum is mainly used as the alkali-soluble alloy component, but other metals like zinc and silicon can also be used. By bringing an alkaline medium into contact with the alloy, the leachable components are dissolved out and often a catalytically active material is obtained. However, Raney catalysts in powder form have the disadvantage that they have to be separated from the reaction medium after the catalytic conversion in continuous and batch processes. This requires time and is costly. Other shapes have therefore been used. For example, JP 07206737 A2 describes the use of spherical Raney catalysts based on copper, which preferably also contain iron, and as leachable component, aluminum. The method can be run using a fixed catalyst bed.

Several attempts have been made to come up with improved, from the point of view of the immobilization of the active phase, or at least alternative Raney catalysts. Since it was found that a serious disadvantage lies in the high bulk density of Raney catalysts and therefore relatively low activity with respect to the weight of the catalytically active metal that is used, attempts have been made to lower the bulk density.

Metal catalysts in the form of hollow bodies, preferably in the form of hollow spheres, are described in DE 199 33 450 A and U.S. Pat. No. 6,747,180 B2.

U.S. Pat. No. 6,486,366 B1 describes the use of Raney catalysts in the form of hollow bodies for producing alcohols by hydrogenation of carbonyl compounds. For the production of the catalysts used, a mixture of an alloy powder of a catalytically active metal and a leachable metal, preferably aluminum, an organic binder and optionally an inorganic binder, water and promoters is deposited onto spheres that consist of a thermally removable material. Preferably, polystyrene foam spheres can be used. The deposition of the mixture containing the metal alloy onto the polymer spheres can preferably be carried out in a fluidized bed. The coated polymer foam spheres are calcined at high temperature in order to remove the polymer foam thermally and to anneal the metal. After calcination the hollow spherical bodies are activated by treatment with caustic solutions, preferably alkali or alkaline earth hydroxides in water, to obtain a catalytically active material.

The same inventors indicated in US 2009/0018366 A1 that this technology can be applied to a wide range of hollow bodied objects and not only spheres, but noted also that the disadvantage of this technology is the increased difficulty of producing the activated hollow spheres. In particular, the production of activated hollow spheres can be critical between the time the styrofoam carrier has been burnt out and the remaining metallic shell containing the alloy is stabilized. It is therefore suggested in US 2009/0018366 A1 to produce instead a supported metal catalyst wherein the support is coated with an alloy containing substance to form a coated support. Although numerous supports are mentioned, metallic foams are even not mentioned.

B. Monnerat, L. Kiwi-Minsker, A. Renken in Chemical Engineering Science, Vol. 56 (2001) pages 633-639, describe hydrogen production by catalytic cracking of methane over nickel gauze under periodic reactor operation. In order to increase the specific surface of bulk Ni metal, a Raney-type layer was formed on the outer surface of the Ni gauze. To this end, an Al—Ni alloy was formed on the Ni-gauze surface and Al selectively removed from the alloy by an aqueous solution of potassium hydroxide. The outer layer surface is mentioned as having the properties of Raney nickel. No details on the alloy formation are mentioned.

CN 101 549 297 A discloses a preparation method of a fixed bed Raney nickel catalyst. To this end, nickel foam is put into an organic solvent followed by cleaning with a diluted acid solution, washing and drying, and metallic aluminum is melted at 660 to 800° C. under an inert atmosphere. The pre-treated nickel foam is then immerged for 0.5 to 6 hours into the melted aluminum whereby the temperature is kept at 660 to 800° C., followed by naturally cooling at room temperature. By controlling the immersion time and the immersion temperature a desired loading of aluminum can be achieved. The obtained foam is then immerged in a NaOH or KOH solution for leaching. The so obtained Raney nickel catalyst shows catalytic activity with a borohydride conversion rate up to 90%.

CN 101 537 360 A discloses a preparation method of a fixed bed Raney nickel catalyst. The method comprises an electroplating process, whereby an aluminum sheet is used as anode and nickel foam as cathode. The aluminized nickel foam is heated at 600 to 1100° C. for 0.5 to 3 hours under an inert gas atmosphere. Leaching with a NaOH or KOH solution is carried out.

CN 101 537 361 A discloses also a preparation method of a fixed bed Raney nickel catalyst which involves a thermal spraying method including flame spraying, arc spraying or plasma spraying. The aluminum coated nickel foam is then heated at 660 to 1100° C. for 0.1 to 5 hours under an inert gas atmosphere. Moreover, leaching with a NaOH or KOH solution is carried out.

U.S. Pat. No. 2,895,819 A discloses a method for preparing a catalytic metal foam which comprises the steps of melting a metal alloy consisting of nickel and a leachable metal, followed by foaming of the metal alloy and leaching. The obtained catalytic metal foam can then be used as a catalyst for hydrogenation. In Example 1, an alloy of aluminum and nickel is prepared and then foamed by using a foaming agent, followed by leaching with caustic soda solution.

U.S. Pat. No. 6,051,117 A discloses the preparation of metallic foam sheets, which can be used in electrolytic cells or where an electric current is applied. In Example 1, the preparation of a perforated nickel foam is disclosed, whereby an open-cell polyurethane foam sheet has been provided with a nickel electroplate coating, followed by thermal decomposition to remove the PU foam substrate. The resulting reticulate nickel foam sheet had a network of open cell pores and continuously connecting strands, whereby the strands had an average thickness of about 50 μm and the nickel sheet had a weight of about 490 g/m², a cell count of 65 ppi and an average pore diameter of about 390 μm. In Example 4, the perforated nickel foam of Example 1 was coated by fusing aluminum as a sheet in foil form into the porous nickel at a temperature of 660° C., followed by leaching with 15 weight percent NaOH.

US 2008/171218 A1 discloses a method for producing metallic foam bodies. In Example 2, a nickel foam body was coated with 1% aqueous solution of poly (vinyl pyrrolidone)

as a binder and then an aluminum powder mixture was applied in a vibration apparatus, whereby the open-porous property of the structure was substantially maintained. A temperature of 300-600° C. was then applied for 30 minutes, followed by 900-1000° C. for 30 minutes, whereby the temperature treatment was carried out in a nitrogen atmosphere. The obtained metallic foam body had a porosity of 91% and was at least almost made up of nickel aluminide.

An object underlying the present invention is therefore to provide a Raney-type material, i.e. a material in which the surface area has been increased by leaching out one or more components from a starting material, in which a Raney-type surface structure can be designed in a highly controllable manner and which preferably allows its efficient and convenient use as a precursor for a catalyst in a variety of chemical reactions, including an easy separation from reaction products.

This object is achieved by the surface modified metallic foam body, the process for the production of the surface modified metallic foam body and the use of the modified metallic foam body in accordance with the respective independent claims. Preferred embodiments of the surface modified metallic foam body, the process for its production as well as the use thereof are indicated in the respective dependent claims. Preferred embodiments of the foam body, process and use correspond to preferred embodiments of the other invention categories, even when this is not explicitly indicated.

Accordingly, the invention is directed to a surface modified metallic foam body containing an unmodified core and an alloy skin, obtainable by a process comprising the steps:
(a) providing a metallic foam body comprising a first metallic material;
(b) applying a second metallic material which is different from the first metallic material and which contains a first metallic compound that is leachable as such and/or that can be transformed by alloying into a second metallic compound that is leachable and different from the first metallic compound on a surface of the metallic foam body (a), by coating the surface of the metallic foam body with an organic binder and a powder of the second metallic material;
(c) forming an alloy skin of the metallic foam body obtained in step (b) by alloying the first metallic material and the second metallic material; and
(d) treating the alloyed metallic foam body obtained in step (c) with an agent that is capable of leaching out the leachable first and/or second metallic compound from the alloy skin of the metallic foam body, to leach out at least a part of the first and/or the second metallic compound from the alloy skin of the metallic foam body;
wherein the thickness of the alloy skin is in the range of up to 50 µm as determined by electron microscopy.

The first metallic material comprises preferably at least one metal that is capable of forming an alloy with the leachable metallic compound. In general, the first metallic material contains preferably at least one metal that is used in various applications (e.g. catalysis) and that can create leachable alloy phases, for example with aluminum. More preferable, the first metallic material contains at least one metal selected from the group consisting of Ni, Fe, Cr, Co, Cu, Ag, Au, Pt, and Pd. Even more preferably, the first metallic material contains at least one metal selected from among Ni, Cr, Co, Cu, and Ag. The first metallic material can be present as a single metal, for example Ni, or if several metals are present, for example as an alloy containing one or more of these metals which might be composed of one or more intermetallic phases. The first metallic material may however also contain leachable metals like for example Al, Si or Zn.

The second metallic material contains a first metallic compound that is leachable as such and/or that can be transformed by alloying into a second metallic compound that is leachable and different from the first metallic compound. For example, if Al powder that has been spread onto a Ni foam is heated to allow alloying, various Al containing intermetallic species can be formed in an alloying step that differ in their leachability. Herein, the term "metallic compound" is to be interpreted broadly and comprises a single metal and intermetallic compounds. Preferably, the second metallic material contains at least one element selected from the group consisting of Si, Al and Zn. In addition, the second metallic material may also contain one or more of the metals that can be used in the first metallic material. Preferably, the second metallic material contains or consists of Al, in general as the first metallic compound. Particular examples of leachable metallic compounds are Al (aluminum), $Ni_2Al_3$ and $NiAl_3$. Moreover, the second metallic material can contain more than one leachable metallic compound.

Alloying conditions are chosen according to the phase diagrams of the materials involved. For example, in the case of alloying involving Ni and Al, alloying conditions are chosen according to the Ni—Al phase diagram in order to maximize the formation of Al-rich and leachable compounds (i.e. $NiAl_3$ and $Ni_2Al_3$) according to Lei et al. (cf. Applied Catalysis A: General 214 (2001) 69-76).

In a preferred embodiment, the first metallic material contains or consists essentially of Ni and the second metallic material contains or consists essentially of a mixture of Ni and Al. Herein the term "mixture" is to be interpreted broadly and covers alloys or mere physical mixtures. For example, if the mixture of Ni and Al is used in powder form, "mixture" refers to both a powder of the alloy as well as a mixture of an Al and Ni powder. Herein, the term "consists essentially of" refers to the case where promoter elements might also be present in a minor amount to improve desired foam body characteristics.

In an even more preferred embodiment, the first metallic material contains or consists essentially of Ni and the second metallic material consists essentially of Al.

The term "consists essentially of" is to be interpreted such that the presence of a minor amount of other elements, in particular metallic elements, is not excluded.

Namely, promoters, i.e. promoter elements that improve the desired characteristics of the modified metallic foam body may be used, in particular in the alloy skin. Promoters may be for example chromium, manganese, iron, vanadium, tantalum, titanium, tungsten, molybdenum, rhenium and or/metals of the platinum group, germanium, tin, antimony or bismuth. The amount of promoter in the surface modified metallic foam body can vary largely as it depends on the type of promoter and its intended use, but is in general in the range of up to 20 wt.-%, preferably, up to 5 wt.-%, based on the total weight of the alloy skin. For example, if Cr or Mo is used as promoter, their amount is often in the range of from 2 to 3 wt.-%.

The surface modified metallic foam body of the present invention is obtained by modifying the surface of a metallic foam body (a).

Metallic foam bodies are known as such. A metallic foam body which may be used for the purpose of the present invention is not particular limited. Preferably, reticulated metallic foams are used. The morphological characteristics including pore size and shape, strut thickness, area density, foam density, geometric surface area and porosity can vary broadly. Moreover, these metallic foam bodies can be obtained by a variety of methods. For example, an organic polymer foam can be coated with a first metallic material where after the organic polymer foam is removed, for example by burning it off at an elevated temperature or by removing it with a suitable solvent. The coating can be achieved by bringing the organic polymer foam in contact with a solution or suspension that contains the first metallic material. This can be for example conveniently carried out by spraying the organic polymer foam with or by dipping it in a corresponding solution or suspension containing the first metallic material. Alternatively a dry deposition could be carried out by for example chemical vapor deposition of the first metallic material.

In a preferred embodiment of the present invention, the metallic foam body (a) used is obtainable by coating a polyurethane (PU) foam with the first metallic material and then burning off the polyurethane (PU) foam. Coating is preferably effected by an electrolytic deposition of the first metallic material on the polyurethane (PU) foam. To this end, the surface of the polyurethane foam is rendered conductive by a known measure before the electrolytic deposition is being carried out.

For the purpose of the present invention it has been found especially advantageous when the metallic foam (a) has a pore size between 100 and 5000 μm, preferably between 450 and 4000 μm and even more preferably between 450 and 3000 μm, and a strut thickness in the range of from 5 to 60 μm, preferably 10 to 30 μm, an apparent foam density in the range of from 300 to 1200 kg/m$^3$, a specific surface area in the range of from 100 to 20000 m$^2$/m$^3$, preferably 1000 to 6000 m$^2$/m$^3$, and a porosity in the range of from 0.50 to 0.95.

The pore size is determined in general by a Visiocell analysis method from Recticel that is described in "The Guide 2000 of Technical Foams", Book 4, Part 4, pages 33-41. In particular, the pore size is determined with an optical measurement of cell diameter by superimposing calibrated rings, printed on transparent paper, on the selected cell. The pore size measurement is performed at least for hundred different cells in order to obtain an average cell diameter value.

The apparent density is determined as weight per volume unit according to ISO 845.

The determination of the surface area of foams considers in general the fact that the lower limit of experimentally determining BET surfaces is about 0.01 m$^2$/g whereby the error margin is about 0.005 m$^2$/g. Thus, in general the surface area of foams involving smaller surface areas requires the use of numerical methods as an approximation wherein the numerical methods are based on specific assumptions.

Thus, the geometrical surface area (GSA) of base foams was determined by using 2-D foam scans and numerical methods. In particular, the GSA was determined by using an imaging technique in a following way: A foam sample (20×20 mm) with hardener (mixture of resin and epoxy hardener in 10:3 weight ratio) is placed in a holder. The sample is hardened for 30 min at 70° C. oven temperature. The foam sample is polished by using a polishing disk and water. Image capture and processing is done with "Inner View" software. Images are captured from 36 districts (one district is 1.7×2.3 mm) and analysis of the captured images is done with the software. Three maximum and three minimum are removed and GSA evaluation is done based on 30 districts according to the equation $$(A_s/V) = \Sigma_i(P_s/A_{total})_i/I$$

Cross-sectional area ($A_{total}$)
Strut area per cross-sectional area (As)
Perimeter with strut per cross-sectional area (Ps)

The specific surface area (BET) of modified foam bodies is determined in accordance with DIN 9277 via gas adsorption.

The porosity (in %) is calculated by the following equation:

$$\text{Porosity (\%)} = 100/VT \times (VT - W(1000/\rho)),$$

wherein VT is the foam sheet sample volume, unit [mm$^3$]; W is the foam sheet sample weight, unit [g] and ρ is the density of the foam material.

The strut thickness was obtained as an average value by using X-ray micro-tomography according to Salvo et al. (cf. Salvo, L., Cloetens, P., Maire, E., Zabler, S., Blandin, J. J., Buffière, J. Y., Ludwig, W., Boller, E., Bellet, D. and Josserond, C. 2003, "X-ray micro-tomography as an attractive characterization technique in materials science", *Nuclear Instruments and Methods in Physics Research* B 200 273-286), which provides 3D visualization of foam microstructure. For each strut, an equivalent hydraulic diameter (diameter equal to a cylinder of the same cross section) is calculated and statistically averaged over a large number of struts. The strut thickness is then obtained from the hydraulic diameters according to the aforementioned method of Salvo et al. as follows, whereby Ni foam is used as an illustrative example:

Foam area density (AD) [kgNi/m$^2$ foam]/Foam thickness (FT) [m]=$X$ (kgNi/m$^3$ of foam)

$X$ [kgNi/m$^3$ of foam]/Nickel density [kgNi/m$^3$ of solid Ni]=$Y$ [dimensionless]

Geometric Surface Area (GSA)=m$^2$/m$^3$

Thickness of foam strut [m]=$Y$/GSA

An illustrative example for 580 μm Ni foam is as follows:

AD=450 g/m$^2$; FT=0.0017 m; Nickel density=8900 kg/m$^3$; GSA=3100 m$^2$/m$^3$

450 [gNi/m$^2$]/0.0017 [m]=265 kgNi/m$^3$ of foam

265 [kgNi/m$^3$ of foam]/8900 [kg/m$^3$ of solid Ni]=0.03 m$^3$ of solid Ni/m$^3$ of foam 1 m$^3$ of foam has a surface area of 3100 m$^2$ Strut thickness of solid Ni [m]=0.03/3100 [m$^2$/m$^3$]= ~10 microns The alloyed metallic foam obtained in step (c) and the surface modified metallic body of the present invention contain an unmodified core and an alloy skin. The core of the surface modified metallic body of the present invention consists preferably of a metallic foam having a pore size between 100 and 5000 μm, preferably between 450 and 4000 μm and even more preferably between 450 and 3000 μm, and a strut thickness in the range of from 5 to 60 μm, preferably 10 to 30 μm, an apparent density in the range of from 300 to 1200 kg/m$^3$, a geometric surface area in the range of from 100 to 20000, preferably 1000 to 6000 m$^2$/m$^3$, and a porosity in the range of from 0.50 to 0.95.

The surface modified metallic foam body has preferably a specific surface area (BET according to DIN 9277, using foam samples of up to 2 g) of 1 to 150 m$^2$/g, and more preferably of 10 to 100 m$^2$/g of the modified foam in the surface region.

The surface modified metallic foam of the present invention shows especially advantageous properties when the thickness of the alloy skin is in the range of up to 50 μm, preferably of from 5 to 50 μm, more preferably of from 5 to 30 μm, and even more preferably in the range of from 5 to 20 μm. This provides for an optimum balance between the mechanical stability of the surface modified metallic foam and desired surface properties, for example catalytic properties.

In general, the thickness of the alloy skin is related to the strut thickness. In this regard it is preferable, when the alloy skin has a thickness of 5 to 70%, preferably 40 to 60% and even more preferably 45 to 55% of an average 30 μm strut thickness.

In another aspect, the present invention is directed to a process for the production of a surface modified metallic foam body containing an unmodified core and an alloy skin, comprising the steps:

(a) providing a metallic foam body comprising a first metallic material;
(b) applying a second metallic material which is different from the first metallic material and which contains a first metallic compound that is leachable as such and/or that can be transformed by alloying into a second metallic compound that is leachable and different from the first metallic compound on a surface of the metallic foam body (a), by coating the surface of the metallic foam body with an organic binder and a powder of the second metallic material;
(c) forming an alloy skin of the metallic foam body obtained in step (b) by alloying the first metallic material and the second metallic material; and
(d) treating the alloyed metallic foam body obtained in step (c) with an agent that is capable of leaching out the leachable first and/or second metallic compound from the alloy skin of the metallic foam body.

In the present process, a metallic foam body (a) is preferably used that has pore sizes between 100 and 5000 μm, more preferably 450 and 3000 μm and a strut thickness in the range of from 5 to 60 μm. Moreover, the alloy density is preferably in the range of from 5000 to 8000 kg/m$^3$ with an apparent foam density being in the range of from 300 to 1200 kg/m$^3$. The geometric surface area of preferred metallic foam is in the range of from 100 to 20000 m$^2$/m$^3$, preferably 1000 to 6000 m$^2$/m$^3$, and the porosity in the range of from 0.50 to 0.95.

The thickness of the alloy skin is preferably in the range of up to 50 μm as determined by electron microscopy.

The terms "leachable" and "leachable metallic compound" are to be understood broadly. Any metallic compound that can be removed, i.e. leached out, by the interaction with a suitable chemical medium is included. For example, in the case of metallic compounds of Al and Ni, $Ni_2Al_3$ and $NiAl_3$ are considered to be leachable metallic compounds whereas NiAl is not considered to be a leachable metallic compound. A suitable chemical medium, i.e. an agent (in the following the term "leaching agent" is also used) that is capable of leaching out the leachable metal, can be an acidic, alkaline or complexing medium. "Complexing medium" refers here to a medium that comprises a complexing agent for the leachable metal.

In the present invention it is however preferred to use alkaline media. Preferably, NaOH, KOH and LiOH or any mixture thereof is used, preferably in the form of an aqueous solution. The concentration of the leaching agent as well as the duration and temperature for its use may vary depending on the first metallic material and the second metallic material.

A preferably used alkaline medium is a 1 to 10 M aqueous solution of NaOH. The leaching step, i.e. step (d), is generally carried out at a temperature between 20 and 98° C., preferably at a temperature between 50 and 95° C. for a period of 1 to 15 minutes, preferably 2 to 10 minutes. For example, in the case where the leachable metallic compound contains or consists of Al, a 5 M solution of NaOH at 90° C. for 3 to 5 minutes may be used advantageously for the leaching step.

The application of a second metallic material in step (b) can be performed by many different methods, such as rolling or dipping the metallic foam body (a) in the second metallic material, or spraying or pouring the second metallic material onto the foam body (a), preferably in the form of a powder. In any way, the application of a second metallic material is done by coating the surface of the metallic foam body (a) with an organic binder and a powder of the second metallic material.

The best method is to apply the second metallic material onto the support foam by spraying or pouring a powder on the support when the support is for example conveyed on a belt. Preferably, the second metallic material is used in the form of a powder with an average particle size in the range of from 30 to 50 μm.

In the process of the invention, in step (b) the surface of the metallic foam body (a) is thus coated with an organic binder and a powder of the second metallic material. And more preferably, the coating of the binder is preferably effected before the coating of the second metallic material.

The binder is usually used in an amount such that the thickness of the binder layer on the foam body is usually in the range of from 10 to 60 μm, preferably 10 to 30 μm.

A particular advantage of the present invention is that the structure of the surface modified metallic foam can be designed in a predictable manner. This can be achieved for example by a proper choice of the first metallic material and the second metallic material. In particular, the choice of the second metallic material allows to control the leachability and hence the morphology of the finally obtained alloy skin.

In a preferred process, an alloy (c) with a desired leachability of the leachable metal is obtained by adjusting an alloying temperature and time as well as a quenching temperature and time.

Preferably, the composition of the second metallic material is adjusted to have a specific leachability. It is moreover preferable to control the composition of the alloy formed in step (c) such that the leaching properties can be controlled to obtain a desired porous surface structure wherein alloying at an elevated temperature is performed followed by a quenching step in order to obtain a surface alloy zone that shows a specific behavior upon leaching.

The second metallic material is preferably composed of 0-80 wt.-% of one or more non-leachable metals and 20-100 wt.-% of one or more leachable, preferably alkali-leachable, metallic compounds, preferably Al. For example, in the case of Al and Ni as metallic elements which constitute the second metallic material, their respective amounts on a weight basis are preferably equal.

The conditions, in particular temperature conditions, will depend on the nature of the second metallic material.

If Al is used as the second metallic material, the forming of an alloy of the first metallic material and the second metallic material as an alloy skin of the metallic foam body is preferably formed by heating the metallic foam obtained in step (b) up to a temperature range of 650 to 730° C., preferably up to a temperature range of from 660 to 710° C.

If a NiAl powder is used as the second metallic material, the upper temperature is significantly higher, namely 850 to 900° C. and preferably 880 to 900° C.

Even more preferably, during the heating to obtain an alloy, the temperature is continuously increased to the aforementioned ranges and is maintained for a holding time of up to 15 min, for example in a temperature range of from 660 to 710° C. when Al is used as the second metallic material. Then the coated and heated metallic foam is cooled. This can be achieved by allowing the metallic foam to cool down, for example to room temperature, by merely stopping the heating. Preferably however, the cooling is assisted by the proper application of a cooling medium. Thus, the ratio of leachable and unleachable metallic components in the formed alloy can be adjusted.

Cooling media can be gases like for example argon or nitrogen or liquids such as for example water, preferably de-gassed water. Among the cooling media, the use of a liquid is preferred.

In a further preferred process the first metallic material comprises or consists of nickel and the second metallic material comprises aluminum.

The presence of promoters might be advantageous. Thus, in a preferred embodiment of the process at least one promoter element is applied in step (b) to the surface of the foam body (a) and/or in an additional step (e) to the foam body obtained in step (d).

The surface modified metallic foam body of the present invention may be used in many chemical and physical processes.

The physical processes are in particular adsorption or absorption processes. Examples are the removal and recovery of metals from the liquid waste streams in pharmaceutical, refining and industrial applications.

The surface modified metallic foam body of the present invention can also be used as a component in catalyst formulations for numerous catalyzed chemical reactions which involve in particular organic compounds, for example hydrogenation, isomerization, hydration, hydrogenolysis, reductive amination, reductive alkylation, dehydration, oxidation, dehydrogenation, rearrangement and other reactions.

The invention is thus directed in a third aspect to the use of the modified metallic foam body of the present invention in an adsorption or absorption process or as a component for a catalytically active material in a chemical process. Preferably, the chemical process is the hydrogenation of a chemical compound.

A very preferred use of the surface modified metallic foam body as a component in the final catalyst formulation is the use in a selective hydrogenation process of carbonyls, olefins, aromatic rings, nitriles, nitro compounds, etc. In principle, the surface modified metallic foam bodies can be used for all Raney-type hydrogenation reaction. Concrete examples are the hydrogenation of nitro groups to amines, the hydrogenation of carbonyl groups, the hydrogenation of polyols, the hydrogenation of fatty nitriles to fatty amines, reductive alkylation, hydrogenation of nitriles to amines, dehydrogenation of alcohols, reductive alkylation, hydrogenation of olefins to alkanes, and the hydrogenation of azide and olefin. The chemical process is preferably the hydrogenation of carbonyl compounds.

In this regard it is to be noted that the surface modified metallic foam body of the present invention easily allows to be tailored to the needs of a specific chemical process. Since the surface modification as described herein can be achieved easily, it is possible to obtain for example catalytically active surface modified metallic foam bodies with differing catalytic activity. By combining several of these metallic foam bodies a catalytically active material can be obtained in which the catalytic activity can be adjusted as needed. It is for example known that the temperature profile in a chemical reactor might not be uniform. The invention allows in this case, that a catalytically active material with a correspondingly adjusted local catalytic activity can be provided by combining metallic foam bodies with suitably adjusted catalytic activities. For example, the catalytic activity might increase from the wall to the interior of a chemical reactor to account for a lower temperature in the interior of the chemical reactor.

The surface modified metal foam bodies of the present invention show a high porosity, are light weight and have a large surface area. Moreover, they reveal a good structural homogeneity in each of the modified alloy skin and the unmodified metallic foam body comprising the first metallic material. As regards flow, mass and heat transfer characteristics, the surface modified metal foams allow a low pressure drop, an enhanced flow mixing, high heat transfer and mass transfer rates, high thermal conductivity and a low diffusion resistance due to the thin modified layer.

The invention has several advantages. The invention allows to produce components for a catalyst to be used in a chemical process with a high mechanical stability and a very defined surface structure of the activated outer layer and a high level of porosity. Moreover the invention allows a relatively high percentage of activated material and a high amount of active surface area in relation to the catalyst's total volume. The surface modified metallic foam body of the present invention enables in this regard good material transfer through it while the transferred material can come into contact with catalytic sites. Moreover, the use of the foam body of the present invention allows avoiding channeling. Since the process of the invention allows a better leaching, the surface modified metallic foam body of the present invention can in embodiments of the present invention also be formed in a convenient manner in situ in a chemical reactor.

The following examples serve to illustrate the invention and may not be construed to limit the present invention.

EXAMPLE 1

A Ni foam body with dimensions of 75 mm×75 mm×1.7 mm with a surface area of 0.0222 $m^2/g$, corresponding to a surface area density of 450 $g/m^2$ and pores with a medium pore size of 580 μm and a porosity of 93.8%, a strut thickness of 10 μm, an apparent density of 552 $kg/m^3$, and a geometrical surface area (GSA) of 3100 $m^2/m^3$ was sprayed with a 1 wt.-% aqueous solution of polyvinylpyrrolidone as binder. The binder was used in an amount to obtain a final layer with a thickness of the polyvinylpyrrolidone of 15 μm.

After drying the sprayed Ni foam body at room temperature, the binder coated foam body was coated with an Al powder with an average particle diameter of from 30 to 50 μm. To this end, Al powder was poured on the binder coated foam body in an amount such that the weight ratio powder/foam was "1". The coated metallic foam was vibrated such that the Al powder could be uniformly distributed on the open-porous structure.

The binder was then removed by heating in a hydrogen atmosphere with a heating rate of 5 K/min up to 600° C. The temperature was then kept at 600° C. for 0.5 hours.

A Ni—Al alloy was then formed by heating continuously with a heating rate of 5 K/min to a temperature of 700° C. After reaching this temperature, the heated foam body was then cooled to room temperature by natural cooling. In this way it was possible to obtain a 50:50 mol-% Ni:Al composition layer on the foam body.

The cooled foam body was then treated with a 5 M solution of NaOH at 70° C. for 3 to 5 minutes.

As a result a surface modified metallic foam body was obtained. The obtained surface modified metallic foam body had an alloy skin with a thickness of up to 10 μm and a specific (BET) surface area of 57.4 m$^2$/g as determined via BET measurement in accordance with DIN 9277 via gas adsorption.

EXAMPLE 2

Unless specified otherwise, Example 1 was repeated with the difference that a NiCrAl foam (73 wt. % Ni, 21 wt. % Cr and 6 wt % Al) was used. Moreover, alloying was effected in an Ar atmosphere at 900° C. for 30 minutes.

A NiCrAl foam body with dimensions of 75 mm×75 mm×1.7 mm with a surface area of 0.00084 m$^2$/g, corresponding to a surface area density of 1180 g/m$^2$ and pores with a medium pore size of 580 μm and a porosity of 89.6%, a strut thickness of 15 μm, an apparent density of 821 kg/m$^3$, and a geometrical surface area (GSA) of 6860 m$^2$/m$^3$ was sprayed with a 1 wt.-% aqueous solution of polyvinylpyrrolidone as binder. The binder was used in an amount to obtain a final layer with a thickness of the polyvinylpyrrolidone of 15 μm.

After drying the sprayed Ni foam body at room temperature, the binder coated foam body was coated with an Al powder with an average particle diameter of from 30 to 50 μm. To this end, Al powder was poured on the binder coated foam body in an amount such that the weight ratio powder/foam was "1". The coated metallic foam was vibrated such that the Al powder could be uniformly distributed on the open-porous structure.

The binder was then removed by heating in a hydrogen atmosphere with a heating rate of 5 K/min up to 600° C. The temperature was then kept at 600° C. for 0.5 hours.

A Ni—Al alloy was then formed by heating continuously with a heating rate of 5 K/min to a temperature of 900° C. After reaching this temperature, the heated foam body was kept on this temperature for 30 minutes and then cooled to room temperature by natural cooling.

The cooled foam body was then treated with a 5 M solution of NaOH at 70° C. for 3 to 5 minutes.

As a result a surface modified metallic foam body was obtained. The obtained surface modified metallic foam body had an alloy skin with a thickness of up to 10 μm and a specific surface area (SSA) of 10.8 m$^2$/g as determined via BET measurement in accordance with DIN 9277 via gas adsorption.

The invention claimed is:

1. A surface modified metallic foam body containing an unmodified core and an alloy skin on surface of the unmodified core, obtained by a process comprising the steps:
   (a) providing a metallic foam body, as a core, comprising a first metallic material, wherein the metallic foam body of (a) has an apparent density in the range of from 300 to 1200 kg/m$^3$ as determined as weight per volume unit according to ISO 845;
   (b) applying a second metallic material which is different from the first metallic material of (a) and which contains a first metallic compound that is leachable as such and/or that can be transformed by alloying into a second metallic compound that is leachable and different from the first metallic compound on a surface of the metallic foam body of (a), by coating the surface of the metallic foam body of (a) with an organic binder and a powder of the second metallic material,
      wherein the second metallic material contains Al as the first metallic compound;
   (c) forming the alloy skin by alloying the first metallic material and the second metallic material of step (b) to give an alloyed metallic foam body comprising the core that is unmodified and an alloy skin formed on the surface of the unmodified core; and
   (d) treating the alloyed metallic foam body obtained in step (c) with an agent that is capable of leaching out the leachable first and/or second metallic compound from the alloy skin of the metallic foam body, to leach out at least a part of the first and/or the second metallic compound from the alloy skin of the alloyed metallic foam body;
wherein the thickness of the alloy skin is in the range of up to 50 μm as determined by electron microscopy, and
   wherein the unmodified core of the alloyed metallic foam body comprises pores with a pore size between 100 and 5000 μm as determined by a Visiocell analysis method from Recticel, a specific surface area in the range of from 100 to 20000 m$^2$/m$^3$ as determined in accordance with DIN 9277 via gas adsorption and a porosity in the range of from 0.50 to 0.95 as determined by using the following equation:

$$\text{Porosity } (\%) = 100/VT \times (VT - W(1000/\rho)),$$

wherein VT is the foam sheet sample W is the foam sheet sample weight; and ρ is the density of the foam material.

2. The surface modified metallic foam body according to claim 1, wherein the first metallic material contains at least one metal selected from the group consisting of Ni, Fe, Cr, Co, Cu, Ag, Au, Pt, and Pd.

3. The surface modified metallic foam body according to claim 2, wherein the metal is selected from the group consisting of Ni, Cr, Co, Cu, and Ag.

4. The surface modified metallic foam body according to claim 1, wherein the second metallic material contains Si or Zn as the second metallic compound.

5. The surface modified metallic foam body according to claim 1, wherein the metallic foam body of (a) is obtained by coating a polyurethane foam with the first metallic material and then burning off the polyurethane foam.

6. A process for producing a surface modified metallic foam body containing an unmodified core and an alloy skin on surface of the unmodified core, comprising the steps:
   (a) providing a metallic foam body, as a core, comprising a first metallic material, wherein the metallic foam body of (a) has an apparent density in the range of from 300 to 1200 kg/m$^3$ as determined as weight per volume unit according to ISO 845;
   (b) applying a second metallic material which is different from the first metallic material of (a) and which contains a first metallic compound that is leachable as such and/or that can be transformed by alloying into a second metallic compound that is leachable and different from the first metallic compound on a surface of the metallic foam body of (a), by coating the surface of the metallic foam body of (a) with an organic binder and a powder of the second metallic material, wherein the second metallic material contains Al as the first metallic compound;

(c) forming the alloy skin by alloying the first metallic material and the second metallic material of step (b) to give an alloyed metallic foam body comprising the core that is unmodified and an alloy skin formed on the surface of the unmodified core; and (d) treating the alloyed metallic foam body obtained in step (c) with an agent that is capable of leaching out the leachable first and/or second metallic compound from the alloy skin of the alloyed metallic foam body, wherein the thickness of the alloy skin is in the range of up to 50 μm as determined by electron microscopy, and wherein the unmodified core of the alloyed metallic foam body comprises pores of a pore size between 100 and 5000 μm as determined by a Visiocell analysis method from Recticel, a specific surface area in the range of from 100 to 20000 $m^2/m^3$ as determined in accordance with using the following equation:

$$\text{Porosity } (\%) = 100/VT \times (VT - W(1000/\rho)),$$

wherein VT is the foam sheet sample volume; W is the foam sheet sample weight; and ρ is the density of the foam material.

7. The process according to claim 6, wherein in alloying in step (c) a heating temperature and time as well as a cooling time are adjusted in order to control the leachability of the alloy skin obtained.

8. The process according to claim 6, wherein the first metallic material comprises nickel and the second metallic material comprises aluminum.

9. The process according to claim 6, wherein the step (b) further comprises applying at least one promoter element to the surface of the metallic foam body of (a).

10. A catalyst formulation comprising the surface-modified metallic foam body of claim 1.

11. A hydrogenation process which comprises subjecting a chemical compound to a chemical reaction in the presence of the catalyst formulation of claim 10.

12. The process according to claim 6, wherein the first metallic material consists of nickel and the second metallic material comprises aluminum.

13. The process according to claim 6, which further comprises a step (e) of applying at least one promoter element to the surface of the alloyed metallic foam body obtained in step (d).

14. The surface modified metallic foam body according to claim 1, wherein the second metallic material consists of Al as the first metallic compound.

15. The surface modified metallic foam body according to claim 1, wherein the treatment (d) is carried out at a temperature between 50 and 95° C. for a period of 2 to 10 minutes.

16. The method according to claim 6, wherein the treatment (d) is carried out at a temperature between 50 and 95° C. for a period of 2 to 10 minutes.

17. The surface modified metallic foam body according to claim 1, wherein the second metallic material powder has an average particle size in a range of from 30 μm to 50 μm.

18. The method according to claim 6, wherein the second metallic material power in (b) has an average particle size in a range of from 30 μm to 50 μm.

* * * * *